United States Patent [19]

Miwa et al.

[11] Patent Number: 4,560,654

[45] Date of Patent: Dec. 24, 1985

[54] METHOD FOR PRODUCING L-LYSINE BY FERMENTATION

[75] Inventors: Kiyoshi Miwa, Matsudo; Mahito Terabe, Yokohama; Masaaki Ishida; Hiroshi Matsui, both of Kawasaki; Haruo Momose, Kamakura, all of Japan

[73] Assignee: Ajinomoto Company Incorporated, Tokyo, Japan

[21] Appl. No.: 261,557

[22] Filed: May 7, 1981

[30] Foreign Application Priority Data

May 16, 1980 [JP] Japan ................................. 55-65007

[51] Int. Cl.[4] ....................... C12P 13/08; C12N 15/00; C12N 1/20
[52] U.S. Cl. ................................... 435/115; 435/172.3; 435/253; 435/840; 435/843; 935/60; 935/72
[58] Field of Search ............... 435/115, 172, 840, 843; 935/60, 72

[56] References Cited

U.S. PATENT DOCUMENTS

| | | | |
|---|---|---|---|
| 3,756,916 | 9/1973 | Leavitt | 435/113 |
| 3,825,472 | 7/1974 | Kubota et al. | 435/115 |
| 4,278,765 | 7/1981 | Debabov et al. | 435/317 |
| 4,346,170 | 8/1982 | Sano et al. | 435/172 |

Primary Examiner—Esther M. Kepplinger
Attorney, Agent, or Firm—Oblon, Fisher, Spivak, McClelland & Maier

[57] ABSTRACT

An L-lysine producing microorganism which is constructed by incorporation into a recipient strain of the genus Brevibacterium or Corynebacterium of a hybrid plasmid having inserted therein a DNA fragment which is derived from a donor strain of the genus Brevibacterium or Corynebacterium and which controls resistance to S-(2-aminoethyl)-cysteine and productivity of L-lysine, is useful for the production of high levels of L-lysine by fermentation.

6 Claims, No Drawings

METHOD FOR PRODUCING L-LYSINE BY FERMENTATION

BACKGROUND OF THE INVENTION

1. Field of the Invention

The present invention relates to a method for producing L-lysine by fermentation, and particularly relates to a method for producing L-lysine with a microorganism constructed by a gene recombination technique.

2. Description of the Prior Art

Hitherto, in order to render a wild strain capable of producing L-lysine from carbohydrates, it has been necessary to induce artificial mutants from the wild strain. There are many known lysine-producing artificial mutants. Most of the known lysine-producing mutants are resistant to lysine-analogues such as S-(2-aminoethyl)-cysteine (AEC), and/or require homoserine for growth, and belong to the genus Brevibacterium or Corynebacterium. These microorganisms produce L-lysine in a yield of from 40 to 50%. Examples of recent publications concerning L-lysine production by fermentation are: Japanese Published Unexamined patent application Nos. 9784/1980, 9793/1980, 9559/1980, 9785/1980, 86091/1978, 86090/1978, 86089/1978, 26391/1978, 20490/1978, 9394/1978 and 6486/1978.

It has however, become difficult to increase the yields of L-lysine using the artificial mutation techniques. A need therefore, continues to exist for the development of novel microorganisms capable of producing L-lysine in high yields.

SUMMARY OF THE INVENTION

It is therefore an object of the present invention to provide a method for producing L-lysine in high yield.

This and other objects of the invention, which will hereinafter become more readily apparent, have been attained by providing a method for producing L-lysine which comprises:

(a) culturing in a culture medium an L-lysine producing microorganism which is constructed by incorporating into a recipient strain of the genus Brevibacterium or Corynebacterium, a hybrid plasmid having inserted therein a chromosomal DNA fragment which is obtained from a bacterium of the genus Brevibacterium and Corynebacterium and which controls resistance to S-(2-aminoethyl)-cysteine and productivity of L-lysine, and (b) recovering the L-lysine accumulated in the culture medium.

DETAILED DESCRIPTION OF THE PREFERRED EMBODIMENTS

The DNA donor strains used in this invention are resistant to S-(2-aminoethyl)-cysteine (hereinafter referred to as "AEC") and capable of producing L-lysine. Such strains naturally have chromosomal DNA region which controls resistance to AEC and L-lysine productivity. Various strains resistant to AEC and capable of producing L-lysine are known, for example, in the patent applications mentioned above. Other DNA donor strains can be induced by giving resistance to AEC and productivity of L-lysine especially to, so called "Coryne-form glutamic acid producing bacteria" of the genus Brevibacterium or Corynebacterium, such as:

*Brevibacterium divaricatum:* ATCC 14020
*Brevibacterium flavum:* ATCC 13826
*Brevibacterium immariophilum:* ATCC 14068
*Brevibacterium lactofermentum:* ATCC 13869
*Brevibacterium roseum:* ATCC 13825
*Brevibacterium saccharolyticum:* ATCC 14066
*Brevibacterium thiogenitalis:* ATCC 19240
*Corynebacterium acetoacidophilum:* ATCC 13870
*Corynebacterium acetoglutamicum:* ATCC 15806
*Corynebacterium callunae:* ATCC 15991
*Corynebacterium lilium:* ATCC 15990
*Corynebacterium melassecola:* ATCC 17965
*Corynebacterium glutamicum:* ATCC 13032

Better result can be obtained when L-lysine producer having higher productivity is used as the DNA donor strain. Productivity of L-lysine can be increased by every known method as shown in the patent applications mentioned above.

Vector DNAs are plasmids or phages which are obtainable from the DNA donor strains mentioned above and their mutants, and the derivatives of the plasmid and phage DNAs.

As the recipient strains, although the wild strains of Coryne-form glutamic acid producing bacteria of the genus Brevibacterium or Corynebacterium can be used, it is desirable to use L-lysine producing mutant derived from the Coryne-form glutamic acid producing bacteria to obtain better result. It is convenient also to use, as the recipient, L-lysine auxotrophs derived from the wild strains or from the L-lysine producing mutants mentioned above for selecting strains transformed to L-lysine producers. In the case where an L-lysine auxotroph is used as the recipient, desirably the auxotroph is induced from a parent strain having higher productivity of L-lysine.

Chromosomal DNA is extracted from the DNA donor in a well-known manner and treated with a restriction endonuclease by a well-known method (Biochem. Biophys. Acta 383: 457 (1975)). Various kinds of restriction endonuclease are applicable if the digestion is made partly. The vector DNA is digested also with restriction endonuclease.

The digested chromosomal and vector DNAs are subjected to a ligation reaction with ligase.

Recombination of DNA to prepare the recombinant plasmid can be carried out by incorporating with terminal transferase deoxyadenylic acid and thymidylic acid, or deoxyguanylic acid and deoxycytidylic acid into the chromosomal DNA fragment and cleaved vector DNA, and by subjecting the modified chromosomal and vector DNA to an annealing reaction.

The hybrid DNA thus obtained can be incorporated into the recipient microorganism by known transformation techniques such as $CaCl_2$-method or protoplast method, and the recipients are thereafter allowed to grow for a while to make the transformed characteristics of transformant stable.

The desired transformants are those which possess a hybrid plasmid inserted therein a chromosomal DNA fragment of the DNA donor which fragment controls resistance to AEC and productivity of L-lysine. Such desired transformants can be selected as those which become resistant to AEC and capable of producing L-lysine when the recipient is introduced with the recombinant DNA by the transformation technique mentioned above.

The hybrid plasmid in the desired transformant mentioned above can be incorporated, after extracting it from the transformant, into other recipient strains of this invention such as AEC resistant lysine-producer and homoserine requiring lysine producer.

The L-lysine producing transformant thus obtained can be cultured by conventional manner to let it produce L-lysine, such as at a pH of 6 to 8, and a temperature of 30° C. to 37° C. The cultivation is continued until the production of L-lysine substantially ceases.

The culture medium employed is conventional and contains carbon source, nitrogen source, inorganic ions and when required minor organic nutrient. As the carbon source, glucose, sucrose and crude materials containing these carbohydrates (such as starch hydrolysate and molasses), organic acid such as acetic acid, and alcohol such as ethanol. Gaseous ammonia, aqueous ammonia, ammonium salts and urea can be used as the nitrogen source.

In the method of this invention, higher yield of L-lysine can be obtained by the newly constructed strains than by the DNA donor or recipient used.

Having generally described this invention, a further understanding can be obtained by reference to certain specific examples which are provided herein for purposes of illustration only and are not intended to be limiting unless otherwise specified.

EXAMPLE 1

(1) Preparation of chromosomal DNA possessing genetic information controlling L-lysine production

*Corynebacterium glutamicum* No. 22 (NRRL B-12416), a mutant resistant to AEC and induced from *Corynebacterium glutamicum* AJ 11560 (FERM-P 5485) (NRRL B-12415), was cultured at 30° C. for 3 hours with shaking in 1 l of CMG-medium containing 1 g/dl peptone, 1 g/dl yeast extract, 0.5 g/dl glucose and 0.5 g/dl NaCl (pH was adjusted to 7.2), and bacterial cells in the exponential growth phase were harvested. Chromosomal DNA was extracted by a conventional phenol-method, and 4.0 mg of purified DNA was obtained.

*Corynebacterium glutamicum* AJ 11560 was newly isolated as a suitable strain for the purpose of this invention.

This strain, AJ 11560, was classified to the section III of the genus Corynebacterium described in Bergey's Manual of Determinative Bacteriology (8th edition, 1974). However, taxonomic characteristics of the species belonging to section III are not disclosed in the Manual, but only disclosed the names of species belonging to section III. Therefore, all original reports disclosed in the Manual as to section III are referred to. AJ 11560 was identified with *Corynebacterium glutamicum* described in "Bull. Agr. Chem. Soc. Japan, 22, 176~185 (1958)" and "J. Gen. Appl. Microbiol., 13, 279~301 (1967)".

(2) Preparation of vector DNA

As the vector, the DNA of plasmid pAM 286 (M.W. $3 \times 10^6$ dalton) was prepared as follows:

A strain of *Corynebacterium glutamicum* AJ 11560 harboring the plasmid pAM286 was incubated at 30° C. in 1 l of CMG-medium. After the strain was incubated until the late log phase, the cells were harvested and then lysed by treatment with lysozyme and SDS. The lysate was centrifuged at 30,000 Xg for 30 minutes to obtain a supernatant. After concentrating the supernatant, 60 μg of the plasmid DNA was obtained by fractionation using agarose gel electrophoresis.

(3) Insertion of chromosomal DNA fragment into vector

Ten μg of the chromosomal DNA was treated with the restriction endonuclease XbaI at 37° C. for 10, 30 or 60 minutes, to cleave DNA chains, and then was heated at 65° C. for 5 minutes, respectively. Five μg of the vector DNA was also treated with the restriction endonuclease, XbaI at 37° C. for 1 hour to cleave the DNA completely, and then was heated at 65° C. for 5 minutes.

The digested chromosomal and vector DNAs were mixed and subjected to the ligation reaction by T4 DNA-ligase in the presence of ATP and dithiothreitol at 10° C. for 24 hours. The reaction mixture was then heated at 65° C. for 5 minutes, and two fold volumes of ethanol were added to it. The recombinant DNA which precipitated was recovered.

(4) Genetic transformation with the hybrid plasmid harboring the genetic information controlling lysine production An L-lysine requiring strain, *Corynebacterium glutamicum* No. 97 (NRRL B-12417), which were derived from *Corynebacterium glutamicum* No. 22 by N-methyl-N'-nitro-N-nitrosoguanidine mutagenesis, was cultured in 20 ml of CMG - medium at 30° C. with shaking. Cells in the exponential growth phase were harvested, and "competent" cells having the ability of DNA uptake were prepared by the $CaCl_2$-treatment.

Into the competent cell suspension, the DNA obtained in step (3) was added, and the DNA was incorporated into the cell. After the transformation reaction, the cell suspension was spread on an agar plate containing, 20 g glucose, 10 g $(NH_4)_2SO_4$, 2.5 g urea, 1 g $KH_2PO_4$, 0.4g $MgSO_4.7H_2O$, 50 μg biotin, 200 μg thiamine hydrochloride, 0.01 g $FeSO_4.7H_2O$, 0.01 g $MnSO_4.4H_2O$, 3.0 g AEC.HCl and 20 g agar, per liter, (pH was adjusted to 7.0). The plate was incubated at 30° C. After 4 days incubation, all of the colonies, which appeared and got the productivity of L-lysine and resistance to AEC, were picked up, purified and isolated. Thus, AJ 11575 (FERM-P 5501) (NRRL B-12418) was obtained.

(5) Production of L-lysine by the prepared lysine producing strain

The transformants obtained in step (4) were cultured to test their L-lysine productivity. The DNA-donor strain No. 22 and the recipients strain No. 97 were cultured in the same manner for comparison.

The culture medium contained 10 g/dl glucose, 0.5 g/dl urea, 4.5 g/dl $(NH_4)_2SO_4$, 0.1 g/dl $KH_2PO_4$, 0.04 g/dl $MgSO_4.7H_2O$, 10 mg/dl adenine, 10 mg/dl sodium glutamate, 0.1 mg/l thiamine.HCL 0.5 mg/l biotin, 1 mg/dl $FeSO_4.7H_2O$, 10 mg/dl $MnSO_4.4H_2O$ and 5 g/dl $CaCO_3$ (separately sterilized) and the pH was adjusted to 8.0.

Twenty ml batches of the fermentation medium were placed in 500 ml flasks, inoculated with one loopful inoculum of the test microorganisms, and the cultivation was performed at 31° C. for 70 hours.

The amounts of L-lysine in the supernatant of the fermentation broth were determined by micro-biological assay.

TABLE 1

| Microorganisms tested | Amount of L-lysine accumulated (mg/dl) |
| --- | --- |
| Corynebacterium glutamicum No. 22 | 120 |
| Corynebacterium glutamicum No. 97 | 12 |
| Corynebacterium glutamicum AJ 11575 | 235 |

EXAMPLE 2

(1) Preparation of chromosomal DNA possessing genetic information controlling L-lysine production By the method shown in step (1) of Example 1, 3.5 mg of chromosomal DNA was obtained from *Brevibacterium lactofermentum* No. 27 (NRRL B-12419) derived from ATCC 13869 and resistant to AEC.

(2) Preparation of vector DNA

From *Brevibacterium lactofermentum* ATCC 13869 by the method shown in step (2) of Example 1, 74 µg of a plasmid pAM330 was obtained as the vector.

(3) Insertion of chromosomal DNA fragment into vector

Ten µg of chromosomal DNA obtained in step (1) was digested by the method shown in step (3) of Example 1.

The vector DNA shown in step (2) was also digested by the method shown in step (3) of Example 1. The digested chromosomal and vector DNAs were ligated by the method shown in step (3) of Example 1.

(4) Transformation with the plasmid harboring the genetic information controlling L-lysine production As the recipient, *Brevibacterium lactofermentum* No. 28 (NRRL B-12420) derived from *Brevibacterium lactofermentum* ATCC 13869 and requiring L-lysine, L-methionine and L-threonine for growth was used, and an L-lysine producing transformant AJ 11590 (FERM-P 5518) (NRRL B-12421) was obtained by the method shown in step (4) of Example 1.

(5) Production of L-lysine by the novel L-lysine production

Productivity of L-lysine of the transformant AJ 11590 obtained in step (4) was tested by the method shown in step (5) of Example 1. The results are shown in Table 2.

TABLE 2

| Microorgansims tested | Amounts of L-lysine accumulated (mg/dl) |
| --- | --- |
| Brevibacterium lactofermentum No. 27 | 140 |
| Brevibacterium lactofermentum No. 28 | 8 |
| Brevibacterium lactofermentum AJ 11590 | 189 |

What is claimed is:

1. A method for producing L-lysine by fermentation, which comprises:
   (a) culturing in a culture medium an L-lysine producing microorganism, wherein said microorganism is NRRL B-12418 or NRRL B-12421; and
   (b) recovering the L-lysine which accumulates in the culture medium.

2. The method according to claim 1, wherein the L-lysine producing microorganism is the transformant NRRL B-12418.

3. The method according to claim 1, wherein the L-lysine producing microorganism is the transformant NRRL B-12421.

4. An L-lysine producing transformant, wherein said transformant is NRRL B-12418 or NRRL B-12421.

5. The transformant according to claim 4, having the designation NRRL B-12421.

6. The transformant according to claim 4, having the designation NRRL B-12418.

* * * * *